US012721543B2

(12) United States Patent
Hamilton

(10) Patent No.: US 12,721,543 B2
(45) Date of Patent: Sep. 1, 2026

(54) APPARATUS AND METHODS FOR VIRAL AND BACTERIAL BREATH COLLECTION

(71) Applicant: QUINTRON INSTRUMENT COMPANY, INC., Milwaukee, WI (US)

(72) Inventor: Eric L. Hamilton, New Berlin, WI (US)

(73) Assignee: QuinTron Instrument Company, Inc., New Berlin, WI (US)

( * ) Notice: Subject to any disclaimer, the term of this patent is extended or adjusted under 35 U.S.C. 154(b) by 822 days.

(21) Appl. No.: 18/053,923

(22) Filed: Nov. 9, 2022

(65) Prior Publication Data

US 2023/0148903 A1 May 18, 2023

Related U.S. Application Data

(60) Provisional application No. 63/277,436, filed on Nov. 9, 2021.

(51) Int. Cl.
*A61B 5/097* (2006.01)
*A61B 5/08* (2006.01)
*G01N 33/497* (2006.01)

(52) U.S. Cl.
CPC .............. *A61B 5/097* (2013.01); *A61B 5/082* (2013.01); *G01N 33/497* (2013.01); *G01N 33/4977* (2024.05)

(58) Field of Classification Search
None
See application file for complete search history.

(56) References Cited

U.S. PATENT DOCUMENTS

2004/0077093 A1 4/2004 Par
2007/0203424 A1 8/2007 Kline
2017/0119280 A1* 5/2017 Ahmad ................ A61B 5/0878
2019/0015081 A1 1/2019 Ssenyange

FOREIGN PATENT DOCUMENTS

WO WO2020/053431 3/2020
WO WO2021/041571 3/2021

OTHER PUBLICATIONS

International Search Report dated Apr. 5, 2023 from PCT/US2022/079546; 5 pgs.
Written Opinion dated Apr. 5, 2023 from PCT/US2022/079546; 6 pgs.
International Preliminary Report on Patentability from PCT/US2022/079546 filed Nov. 11, 2022: 8 pgs.

* cited by examiner

*Primary Examiner* — Jay B Shah
(74) *Attorney, Agent, or Firm* — Ryan Kromholz & Manion, S.C.

(57) ABSTRACT

Breath is used to detect the presence of absence of viruses or bacteria in a test subject. A series of devices can be used to collect a breath specimen. The breath specimen is either passed through a liquid or mixed with a liquid, the liquid capturing the viruses or bacteria contained in the breath. Alternatively, the breath specimen passes a filter medium, and the filter medium captures the viruses or bacteria contained in the breath. Liquid is then passed by the filter medium and collected. Liquids captured by these methods can then be tested by a laboratory, for instance using PCR techniques.

7 Claims, 6 Drawing Sheets

APPARATUS AND METHODS FOR VIRAL AND BACTERIAL BREATH COLLECTION

RELATED APPLICATIONS

This application claims the benefit of provisional application Ser. No. 63/277,436 filed 9 Nov. 2021.

BACKGROUND OF THE INVENTION

Virus detection and analysis is a growing industry. Rapid testing methods are required to help detect viruses and bacteria.

Air from the lungs of a person can be used for many different types of testing that would otherwise require the person to undergo an invasive procedure. For example, alveolar air can be analyzed for the noninvasive diagnosis of a wide variety of conditions including the noninvasive diagnosis of stomach infections related to a high incidence of ulcers, enzymatic deficiencies, and metabolic conditions and/or abnormalities. Crucial to any such testing is the ability to get an accurate sample containing a sufficient volume of air representative of true alveolar air, desirable for specific testing.

There are several types of diagnostic tests for detection of viral and bacterial maladies. These include molecular assays such as rapid molecular assays and polymerase chain reaction (PCR) tests, and antigen detection tests.

There are three key steps to common PCR testing: 1) sample collection, 2) extraction, and 3) PCR analysis.

Sample collection is commonly done using a swab to collect respiratory material found for instance in a patient's nose. A swab contains a soft tip on a long, flexible stick that is inserted into the patient's nose. After collection, the swab is sealed in a tube and then sent to a laboratory.

When a laboratory technologist receives the sample, they perform sample extraction, which mixes liquids with the swab to extract the genetic material of any virus that may be on the swab.

The PCR step then tests the liquids from the sample extraction step. In this step, special chemicals and a PCR machine, called a thermal cycler, cause a reaction to occur that makes millions of copies of a small portion of a virus's genetic material. During this process, one of the chemicals produces a fluorescent light if the targeted virus is present in the sample. This fluorescent light is a "signal" that is detected by the PCR machine and special software is used to interpret the signal as a positive test result.

SUMMARY OF THE INVENTION

This invention relates to the field of sampling air from the lungs and specifically to the field of obtaining a sample of a person's breath, filtering the breath through a liquid medium and testing the liquid medium for viruses and bacteria, preferably but not limited to, PCR testing.

Breath is used to detect the presence of absence of a wide variety of viruses or bacteria, such as COVID, the flu, etc. A series of devices can be used to collect breath specimens. The breath specimen is then passed through a liquid or mixed with a liquid, or past a filter media. In the case of a breath specimen passed through a liquid, the liquid captures viruses or bacteria, and the liquid can then be tested, such as by a PCR machine. In the case of a breath specimen presented past a filter media, the filter media can be eluted with a liquid. The collected and processed liquid can then be tested by a laboratory, such as by using PCR techniques.

An apparatus for sampling exhaled breath of a test subject is disclosed, comprising a breath intake structure, a first one-way valve allowing passage of breath through said breath intake structure into an upstream portion of a chamber, a sealed vessel containing a volume of liquid and an evacuated portion, said sealed vessel selectively coupled with said chamber, a breath introduction passage between said upstream portion of said chamber into said volume of liquid in said sealed vessel, and a breath escape passage between said evacuated portion of said sealed vessel to allow said breath to escape said sealed vessel. Optionally, the apparatus further comprises a downstream portion of said chamber selectively coupled to said breath escape passage, and a dividing wall between said upstream and said downstream portions of said chamber. A second one-way valve allowing passage of breath from said downstream portion of said chamber out of said apparatus can be provided.

A method of sampling exhaled breath of a test subject is also disclosed, the method comprising breathing into said breath intake structure, directing the breath through said volume of liquid contained in said sealed vessel and into said evacuated portion of said sealed vessel, sampling said liquid for a presence or an absence of a predetermined malady such as viral or bacterial diseases. Breath is directed from said evacuated portion of said sealed vessel into said downstream portion of said chamber, and optionally, following the step of directing the breath through said volume of liquid contained in said sealed vessel and into said evacuated portion of said sealed vessel, decoupling said sealed vessel from said chamber, removing said liquid from said sealed vessel, sampling said liquid for said predetermined malady using at least one of a rapid molecular assay, a polymerase chain reaction test, and an antigen detection test.

A method of sampling exhaled breath of a test subject is also disclosed in which exhaled breath is exposed to a filter medium, passing liquid through said filter medium, collecting said liquid, sampling said liquid for a predetermined malady using at least one of a rapid molecular assay, a polymerase chain reaction test, and an antigen detection test. Optionally, said filter medium is carried by a structure coupled to a breath intake structure, which can comprise at least one of an expandable bag structure, a vial, and a chamber comprising a breath intake upstream of said filter medium and a breath exhaust downstream of said filter medium.

A method of sampling exhaled breath of a test subject, the method comprising collecting said exhaled breath in a vessel, introducing a liquid into said vessel, mixing said liquid and said exhaled breath, collecting said liquid, sampling said liquid for a predetermined malady using at least one of a rapid molecular assay, a polymerase chain reaction test, and an antigen detection test, which can be introduced into said vessel prior to or after collecting said exhaled breath in said vessel.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
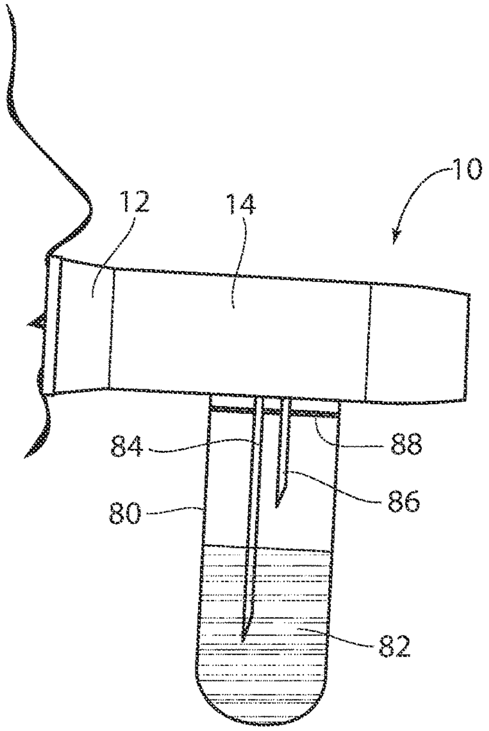
FIG. 1 is a side view of a device for sampling viruses and or bacteria from a breath sample by passing the breath sample through a liquid.
Figure 2:
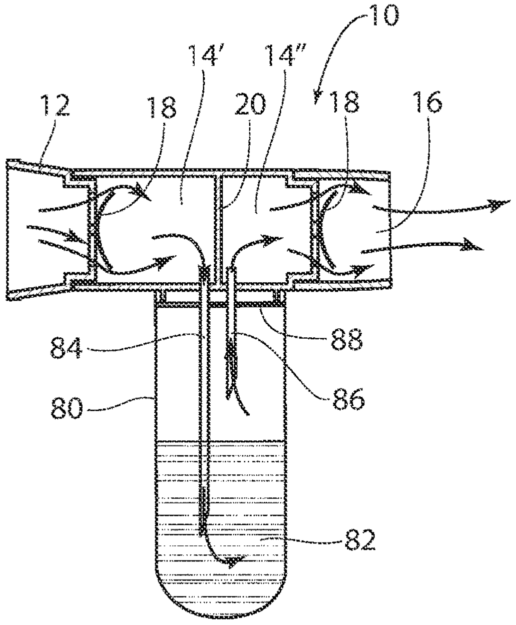
FIG. 2 is a cross-sectional view of the device of FIG. 1.
Figure 3:
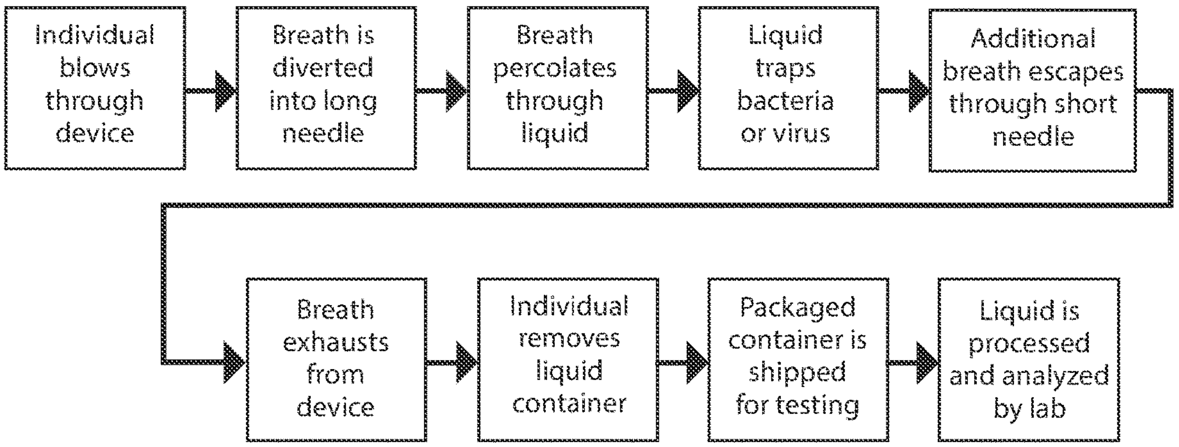
FIG. 3 is a schematic depiction of a method for sampling viruses and or bacteria from a breath sample using the device of FIG. 1.
Figure 4:
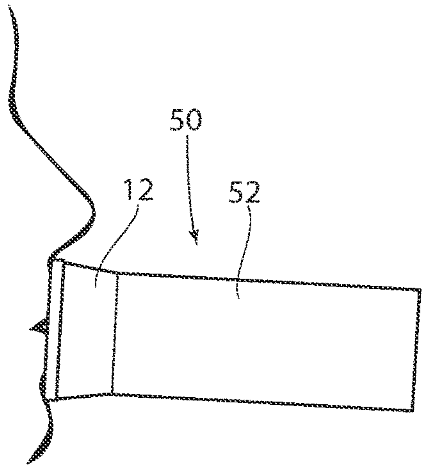
FIG. 4 is a side view of a first alternate device for sampling viruses and or bacteria from a breath sample by passing the breath sample through a filter medium.
Figure 5:
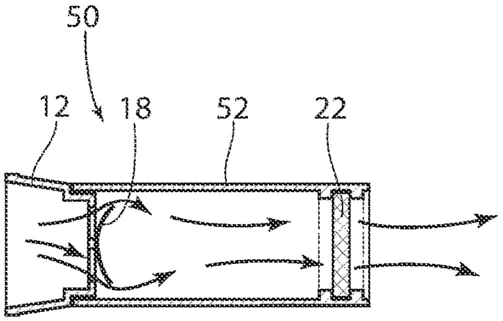
FIG. 5 is a cross-sectional view of the device of FIG. 4.

Referring now collectively to FIGS. 1-3, a side view, a cross-sectional view and a schematic, respectively, of a device 10 for sampling viruses and or bacteria from a breath sample by passing the breath sample through a liquid 82 contained in a vial 80 is shown. A breath intake structure 12 receives breath from an individual. Breath first passes a first one-way flutter valve 18. Breath next enters an upstream portion 14' of chamber 14 (see FIG. 2), the chamber 14 having a dividing wall 20 between the upstream portion 14' and a downstream portion 14" of said chamber. Next, the breath is routed into long needle 84, the tip of which is submersed in liquid 82 contained in otherwise evacuated chamber, or vial 80 having a septum 88. As the breath percolates though liquid 82, the percolated breath escapes through short needle 86 in the headspace of vial 80 and past dividing wall 20, and out a second one-way flutter valve 18, and through discharge chute 16. It is noted that two discrete needles 84 and 86 are shown with a small gap between them. The small gap can be of variable width, or, alternatively, the needles 84 and 86 can be coupled to one another.

Following the percolation of the breath through the liquid 82, the device is removed from self-sealing membrane or septum 88, leaving only liquid 82 and breath/headspace air contained within vial 80. Vial 80 can then be transported for further processing, for example by a PCR machine in a laboratory.

Instead of using a vial 80 pre-supplied with liquid 82, breath can be captured in vial 80, and liquid 82 added later into vial 80, and mixed with the collected breath contained in vial 80. Alternatively, a user would take evacuated vial 80, and elution liquid 82, provided to the user separately, could be drawn into the vial 80. The vial 80, now containing elution mixture 80, would be impaled through septum 88 onto needles 84 and 86.

Figure 12:
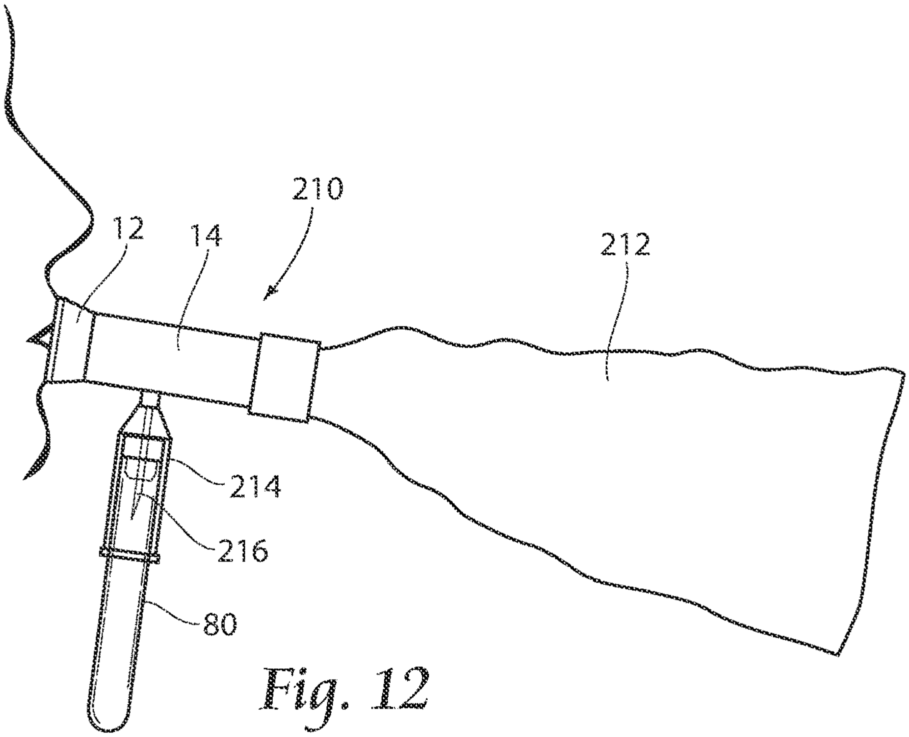
FIG. 12 is a side view of a third alternate device for sampling viruses and or bacteria from a breath sample by passing the breath sample through a filter medium.

In the embodiment shown in FIGS. 1 and 2, it is preferred that needles 84 and 86 be initially be provided with a needle guard (not shown), similar to needle guard 214 as shown in FIG. 12, which would be removed immediately prior to impaling vial 80 onto needles 84 and 86.

A breath testing apparatus such as shown in U.S. Pat. No. 10,413,216, incorporated herein by reference, can be also used to collect a breath specimen as described therein.

Figure 6:
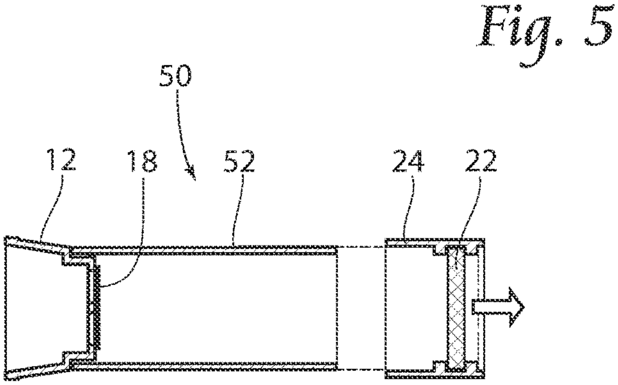
FIG. 6 shows detachment of the filter medium from the breath testing device.
Figure 7:
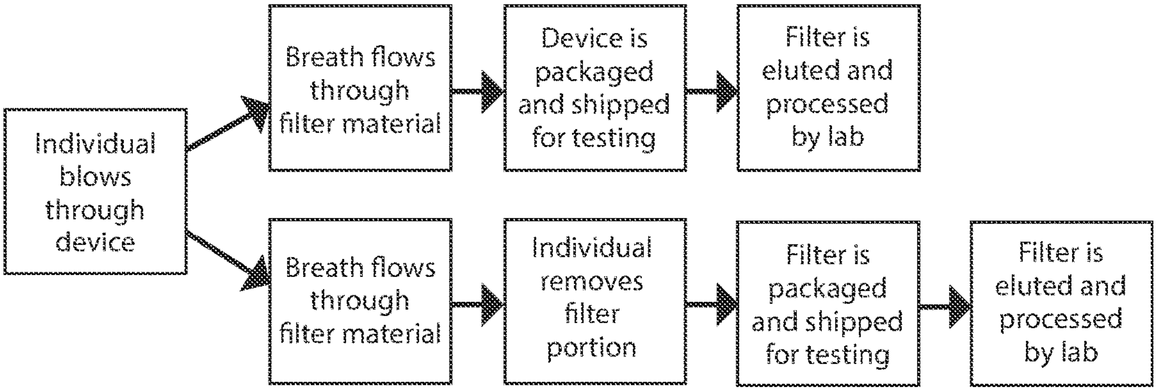
FIG. 7 is a schematic depiction of a method for sampling viruses and or bacteria from a breath sample using the device of FIGS. 4-6.
Figure 8:
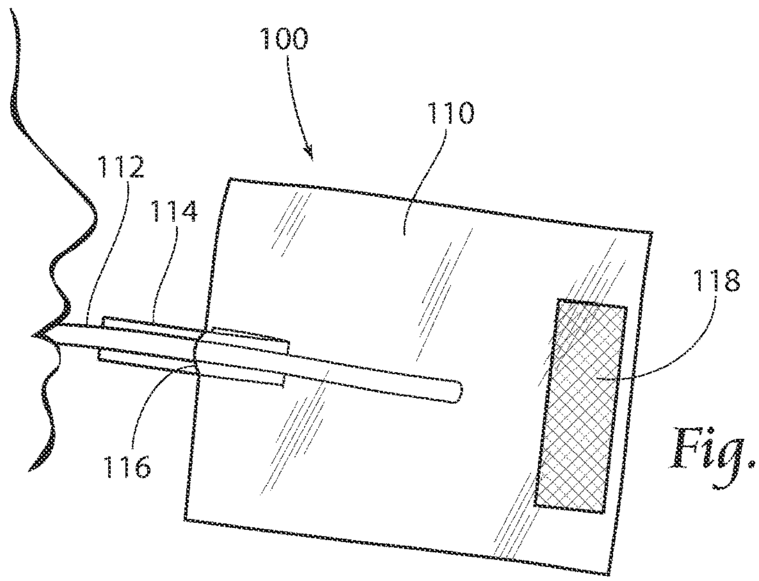
FIG. 8 is a side view of a second alternate device for sampling viruses and or bacteria from a breath sample by trapping the breath sample against a filter medium.
Figure 10:
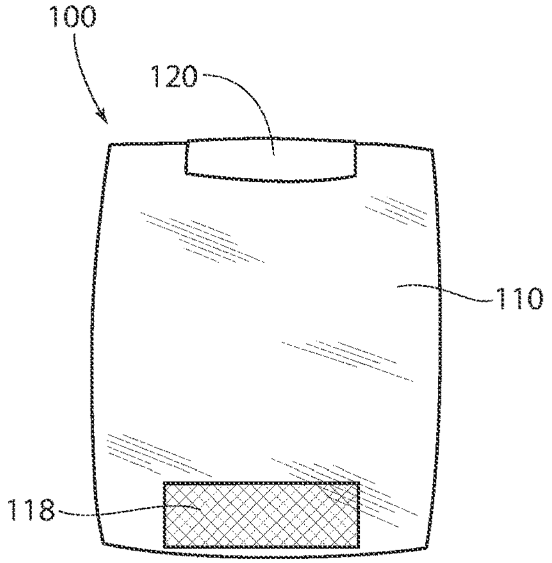
FIG. 10 is a side view of the device of FIG. 8 sealed and prepared for transport.
Figure 9:
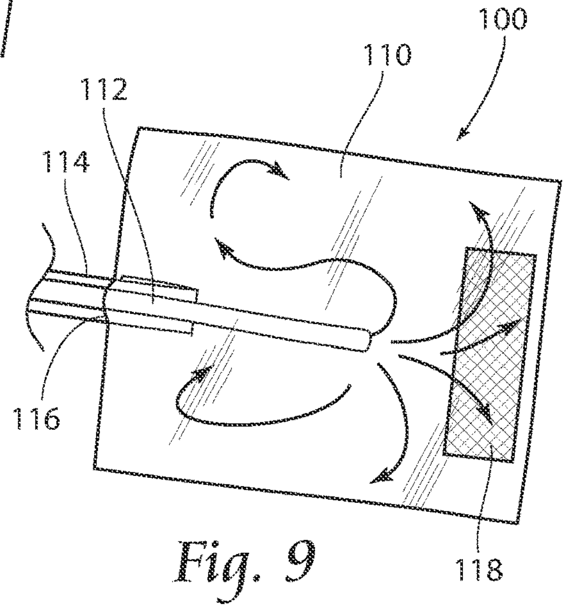
FIG. 9 is a cross-sectional view of the device of FIG. 8.
Figure 11:
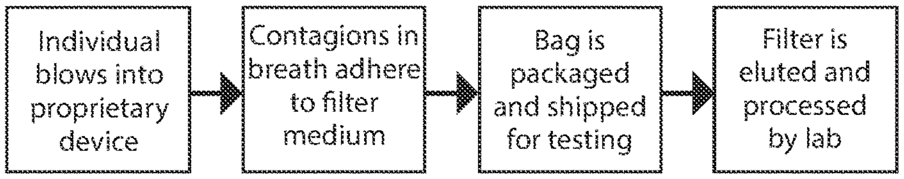
FIG. 11 is a schematic depiction of a method for sampling viruses and or bacteria from a breath sample using the device of FIGS. 8-10.

Referring now to FIGS. 4-7, a side view, a pair of cross-sectional views and a schematic, respectively, of a device 50 is shown. Device 50 is used for sampling viruses and/or bacteria from a breath sample by passing the breath sample through a filter medium 22. Device 50 is a cylindrical tube shape chamber 52 coupled to breath intake structure 12. At the outlet of breath intake structure 12 lies a one-way flutter valve 18, which allows passage of breath into chamber 52. At an outlet of chamber 52 lies filter medium (could be multiple types or styles of filter or medium) 22. Filter medium 22 is inline with the flow of breath (could be within the tube, or on an end for removal after procedure). Breath passes one-way flutter valve 18, and travels through chamber 52 past and across filter medium 22. Referring to FIG. 6, filter medium 22 along with portion 24 of chamber 52 can be removed either by an individual and sent for further processing, or the entire device can be sent for further processing. Whether portion 24 is removed and sent for processing, or the entire device 50 is sent for processing, filter medium 22 would be eluted by a laboratory to process and analyze.

Referring now to FIGS. 8-11, a side view of a second alternate device 100 for sampling viruses and or bacteria from an exhaled breath sample is shown. In this embodiment, the breath sample is trapped against filter medium 118. The air sampling device 100 is comprised of a breath intake structure 112 is used by a test subject to exhale breath into an expandable bag structure 110 through a bag structure inlet 116. The breath intake structure 112 can be constructed of commonly available materials, and a drinking straw may be the preferred breath intake structure 112. The expandable bag structure 110 is preferably constructed of a supple, airtight, gas impermeable, and inert material.

An adhesive patch 114 is adhered to an interior surface of the inlet 116, and the adhesive patch 114 is selectively covered by a removable adhesive patch cover selectively adhered the first side of the adhesive patch 114. The breath intake structure 112 is selectively communicatively coupled with expandable bag structure 110 through the inlet 116, between a second interior surface of the inlet and the removable adhesive patch cover.

The adhesive patch 114 is coextensive with the inlet at one end, and another end extends into the interior of the expandable bag structure 110. The removable adhesive patch cover is at one end coextensive with the adhesive patch first end, and the removable adhesive patch cover extends into the expandable bag structure 110 interior at least to the adhesive patch second end, and the other end of the removable adhesive patch cover extends out of the inlet.

An adhesive inlet seal patch 120 can be provided to supply additional seal to the expandable bag structure 110, beyond the seal provided by the adhesive patch 114. The adhesive inlet seal patch 120 can be labeled with a sample identifier, such as a barcode or machine-readable system. The sample identifier provides a convenient method for sequentially labeling air samples, should the samples include a preloaded desiccant or a chemical indicator, or should samples from different patients be shipped together.

A filter/medium 118 is placed within the bag 110. The user inserts breath intake structure 112 into the bag 110 and blows breath through breath intake structure 112. Any virus/bacteria present in the breath adheres or is trapped within the filter medium 118. After exhalation, the user removes breath intake structure 112, seals the bag 110 with adhesive patch 114 and, optionally, adhesive inlet seal patch 120, and next wipes expandable bag structure 110 with a provided alcohol wipe and then ships expandable bag structure 110 to the laboratory. The laboratory can cut expandable bag structure 110 open and remove the filter medium and perform their preferred elution method and analyze on their preferred device.

Figure 13A:
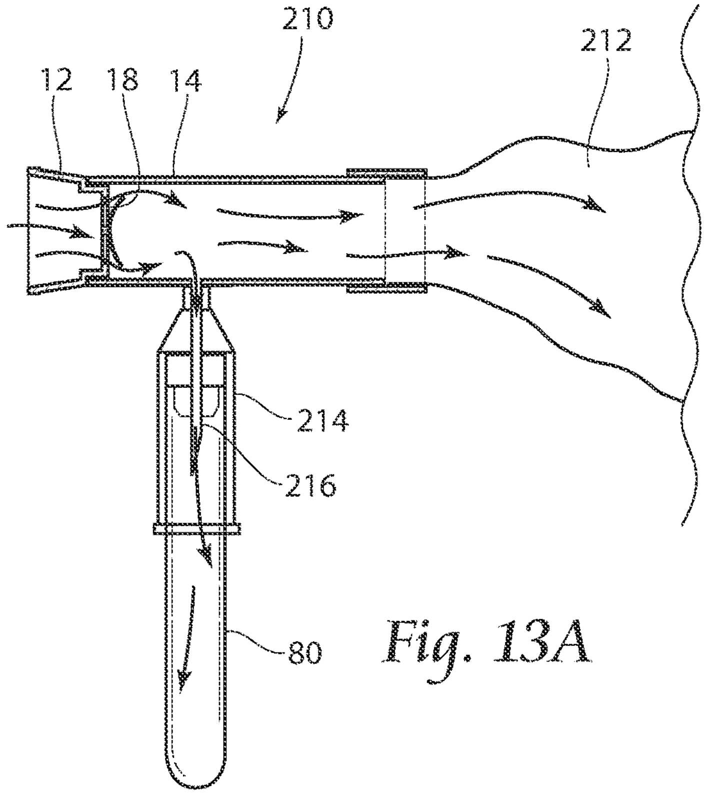
FIG. 13A is a cross-sectional in use view of the device of FIG. 12.
Figure 13B:
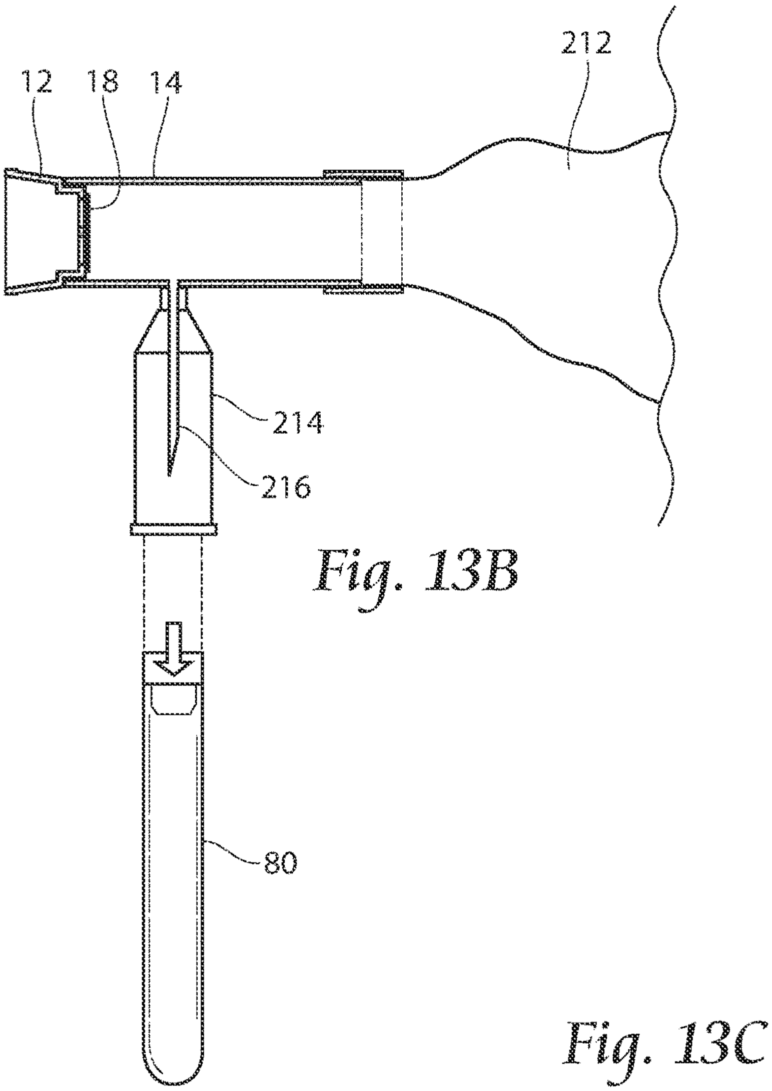
FIG. 13B is a cross-sectional view of the device of FIG. 12, with a liquid containing vessel detached from a breath expulsion vessel.
Figure 13C:
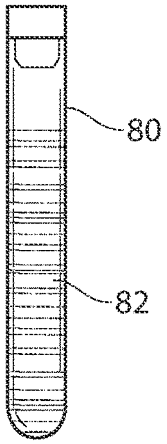
FIG. 13C is a side view of a test tube containing a mixture of breath and liquid.
Figure 14:
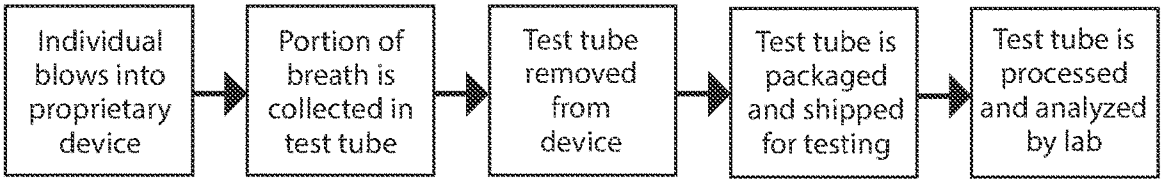
FIG. 14 is a schematic depiction of a method for sampling viruses and or bacteria from a breath sample using the device of FIGS. 12-13C.

Referring now to FIGS. 12-14, a third alternate device 210 for sampling viruses and/or bacteria from a breath sample is shown. In this embodiment, the breath sample is passed into an evacuated container or vial 80 as shown, the vial 80 having a self-sealable septum (not shown) initially impaled onto needle 216. FIG. 13A is a cross-sectional in use view of the device 210 of FIG. 12. FIG. 13B is a cross-sectional view of the device 210 of FIG. 12, with breath containing vessel or vial 80 detached from the remaining components of device 210, following collection of breath using device 210. FIG. 13C is a side view of vial 80 containing a mixture of breath and liquid 82. FIG. 14 is a schematic depiction of a method for sampling viruses and/or bacteria from a breath sample using device 210.

Referring now to FIGS. 12 and 13A, a user breathes into mouthpiece 12. Breath passes one-way flutter valve 18, through chamber 14, and a first portion of breath passes into waste bag 212. As breathing into mouthpiece 12 continues, back pressure builds in waste bag 212, until a second portion of breath (preferably alveolar air) passes into evacuated container or vial 80 through needle 216, the needle 216 protected by needle guard 214.

After the breath sample is collected in vial 80, vial 80 can be separated from the remaining components of device 210. A laboratory can then inject a preferred liquid solution for elution through the septum or self-sealing membrane on vial 80, and next shake vial 80 to mix the headspace air/breath and liquid solution. Alternatively, vial 80 could initially be provided containing the elution liquid 82, or the liquid 82 could be provided to the user in a test kit, the user then injecting liquid 82 into vial 80.

The laboratory can then extract the liquid sample for further processing; e.g., PCR.

Figure 15A:
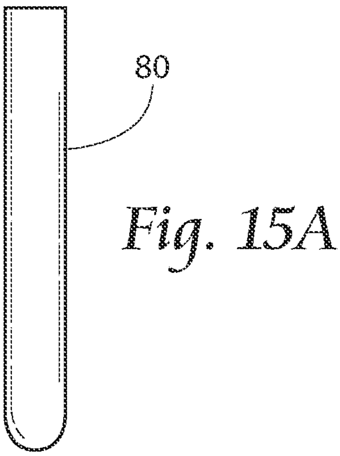
FIG. 15*a* is a side view of a test tube method for sampling viruses and or bacteria from a breath sample.
Figure 15B:
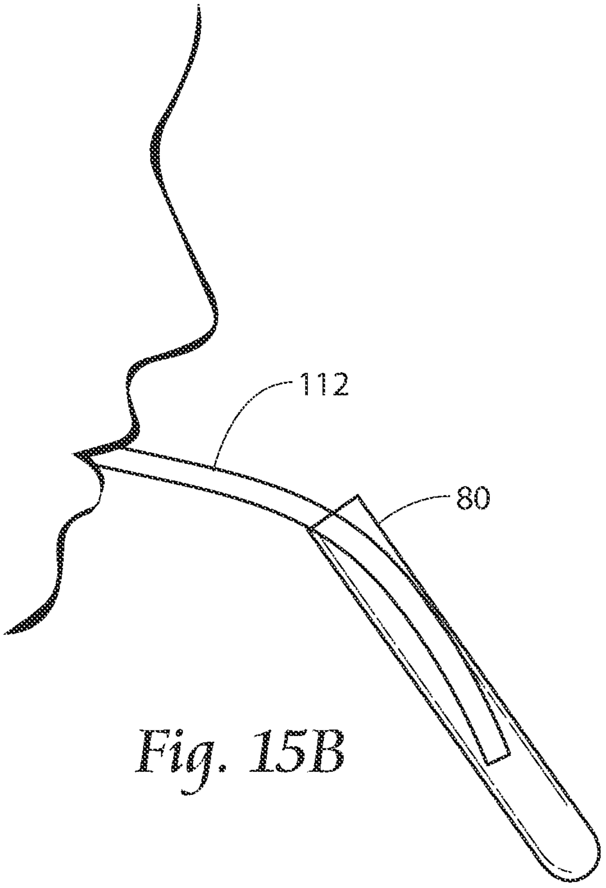
FIG. 15*b* is the device of FIG. 15*a* shown in use, receiving a breath sample.
Figure 15C:
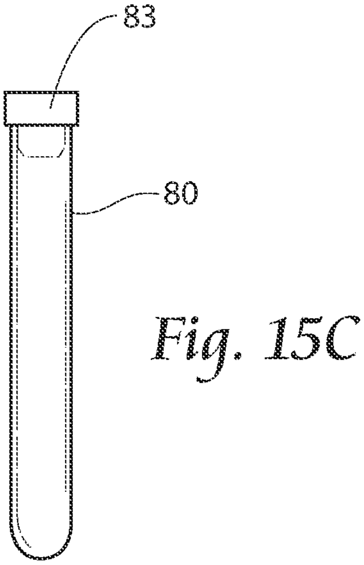
FIG. 15*c* is the device of FIG. 15*a* shown in use, carrying a captured a breath sample.

Referring now to either FIG. 13A or 13B, the container 80 could be pre-coupled Referring now to FIGS. 15A-C, a side view of a test tube method for sampling viruses and/or bacteria from a breath sample is shown. In this embodiment, a user removes a cap 83 (shown in FIG. 15C) from vial 80, and inserts a breath intake structure 112 into vial 80. The user then breathes a full breath through the breath intake structure 112 into the vial 80, removes the breath intake structure 112 and quickly places the cap 83 back on the vial 80.

Still referring to FIGS. 15A, B, and C, as is shown, the elution mixture 82 as described with reference to previous embodiments, is not required to be, but can be, initially within the vial 80.

Also in this embodiment, a laboratory can then inject a preferred liquid solution for elution through a septum on vial 80 and shake the vial 80 to mix the headspace air/breath and liquid solution. Alternatively, a swab (not shown) could be introduced and contained within the vial 80, and then following breath exhalation into the vial 80, the swab could then be removed from the inside of the vial 80, and then an elution mixture could be introduced to the swab. The laboratory can then extract the liquid sample for further processing; e.g., PCR.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. An apparatus for sampling exhaled breath of a test subject, the apparatus comprising:

a breath intake structure;

a first one-way valve allowing passage of breath through said breath intake structure into an upstream portion of a chamber;

a sealed vessel containing a volume of liquid and an evacuated portion, said sealed vessel selectively coupled with said chamber;

a breath introduction passage between said upstream portion of said chamber into said volume of liquid in said sealed vessel, said breath introduction passage comprising a first end positioned within said upstream portion of said chamber, and a second end positioned in said volume of liquid in said sealed vessel;

a breath escape passage between said evacuated portion of said sealed vessel and a downstream portion of said chamber to allow said breath to escape said sealed vessel, said breath escape passage comprising a first end positioned within said downstream portion of said chamber, and a second end positioned in said evacuated portion of said sealed vessel;

a self-sealing membrane carried by said sealed vessel, said breath introduction passage and said breath escape passage positioned through said self-sealing membrane.

2. The apparatus according to claim 1, wherein said downstream portion of said chamber is selectively coupled to said breath escape passage.

3. The apparatus according to claim 2, the apparatus further comprising a dividing wall between said upstream and said downstream portions of said chamber.

4. The apparatus according to claim 2, the apparatus further comprising a second one-way valve allowing passage of breath from said downstream portion of said chamber out of said apparatus.

5. A method of sampling exhaled breath of a test subject using the apparatus of claim 1, the method comprising:

breathing into said breath intake structure;

directing the breath through said volume of liquid contained in said sealed vessel and into said evacuated portion of said sealed vessel;

sampling said liquid for a presence or an absence of a predetermined malady.

6. The method according to claim 5, the method further comprising:

directing said breath from said evacuated portion of said sealed vessel into said downstream portion of said chamber.

7. The method according to claim 6, the method further comprising:

following the step of directing the breath through said volume of liquid contained in said sealed vessel and into said evacuated portion of said sealed vessel, decoupling said sealed vessel from said chamber;

removing said liquid from said sealed vessel;

sampling said liquid for said predetermined malady using at least one of a rapid molecular assay, a polymerase chain reaction test, and an antigen detection test.

* * * * *